(12) United States Patent
Schröder et al.

(10) Patent No.: US 7,385,057 B2
(45) Date of Patent: Jun. 10, 2008

(54) METHOD AND DEVICE FOR PRODUCING MELAMINE IN A SINGLE-PHASE TUBULAR REACTOR

(75) Inventors: Frank Schröder, Naunhof (DE); Johannes Fellner, Steyr (AT); Hartmut Bucka, Eggendorf (AT)

(73) Assignee: AMI Agrolinz Melamine International GmbH, Linz (AT)

( * ) Notice: Subject to any disclaimer, the term of this patent is extended or adjusted under 35 U.S.C. 154(b) by 0 days.

(21) Appl. No.: 10/559,769

(22) PCT Filed: Jun. 1, 2004

(86) PCT No.: PCT/EP2004/005882

§ 371 (c)(1),
(2), (4) Date: Jun. 28, 2006

(87) PCT Pub. No.: WO2004/111016

PCT Pub. Date: Dec. 23, 2004

(65) Prior Publication Data

US 2007/0060751 A1    Mar. 15, 2007

(30) Foreign Application Priority Data

Jun. 12, 2003   (DE) ............... 103 26 827

(51) Int. Cl.
*C07D 251/60* (2006.01)
*C07D 251/62* (2006.01)

(52) U.S. Cl. ...................... 544/201; 544/203

(58) Field of Classification Search ........... 544/201, 544/203

See application file for complete search history.

(56) References Cited

U.S. PATENT DOCUMENTS

| 2,566,223 A | 8/1951 | MacKay |
| 2,644,820 A | 7/1953 | Gresham |
| 2,776,286 A | 1/1957 | Lobdell |
| 7,176,309 B2 * | 2/2007 | Schroder et al. ............ 544/203 |

FOREIGN PATENT DOCUMENTS

| DE | 697 19 850 T2 | 12/2003 |
| EP | 0 747 366 A2 | 12/1996 |
| EP | 0 808 836 A1 | 11/1997 |
| WO | WO 97/34879 | 9/1997 |
| WO | WO 99/00374 | 1/1999 |
| WO | WO 02/12206 | 2/2002 |
| WO | WO 02/34730 | 5/2002 |
| WO | WO 02/051818 A1 | 7/2002 |
| WO | WO 2004085413 A1 * | 10/2004 |

OTHER PUBLICATIONS

Crews et al.; "Melamine and Guanamines"; Ullmann's Enclyclopedia of Industrial Chemistry; 1990; pp. 171-185, vol. A 16; VCH; New York, NY: USA.

* cited by examiner

*Primary Examiner*—Venkataraman Balasubram
(74) *Attorney, Agent, or Firm*—The Webb Law Firm

(57) ABSTRACT

The invention relates to a method and a device for producing melamine by means of the thermal conversion of urea. The invention is characterized in that: a) urea is reacted to form melamine at least partially under reaction conditions wherein an educt, an intermediate and/or an end product are present in a supercritical state; and b) the mixture consisting of at least one educt, an intermediate and/or an end product essentially forms a homogeneous phase and all educts, intermediates, and/or end products are in a complete solution. The single-phase reaction results in an especially efficient reaction.

21 Claims, 3 Drawing Sheets

130 bar

350 bar

600 bar 800 bar

METHOD AND DEVICE FOR PRODUCING MELAMINE IN A SINGLE-PHASE TUBULAR REACTOR

Figure 1:
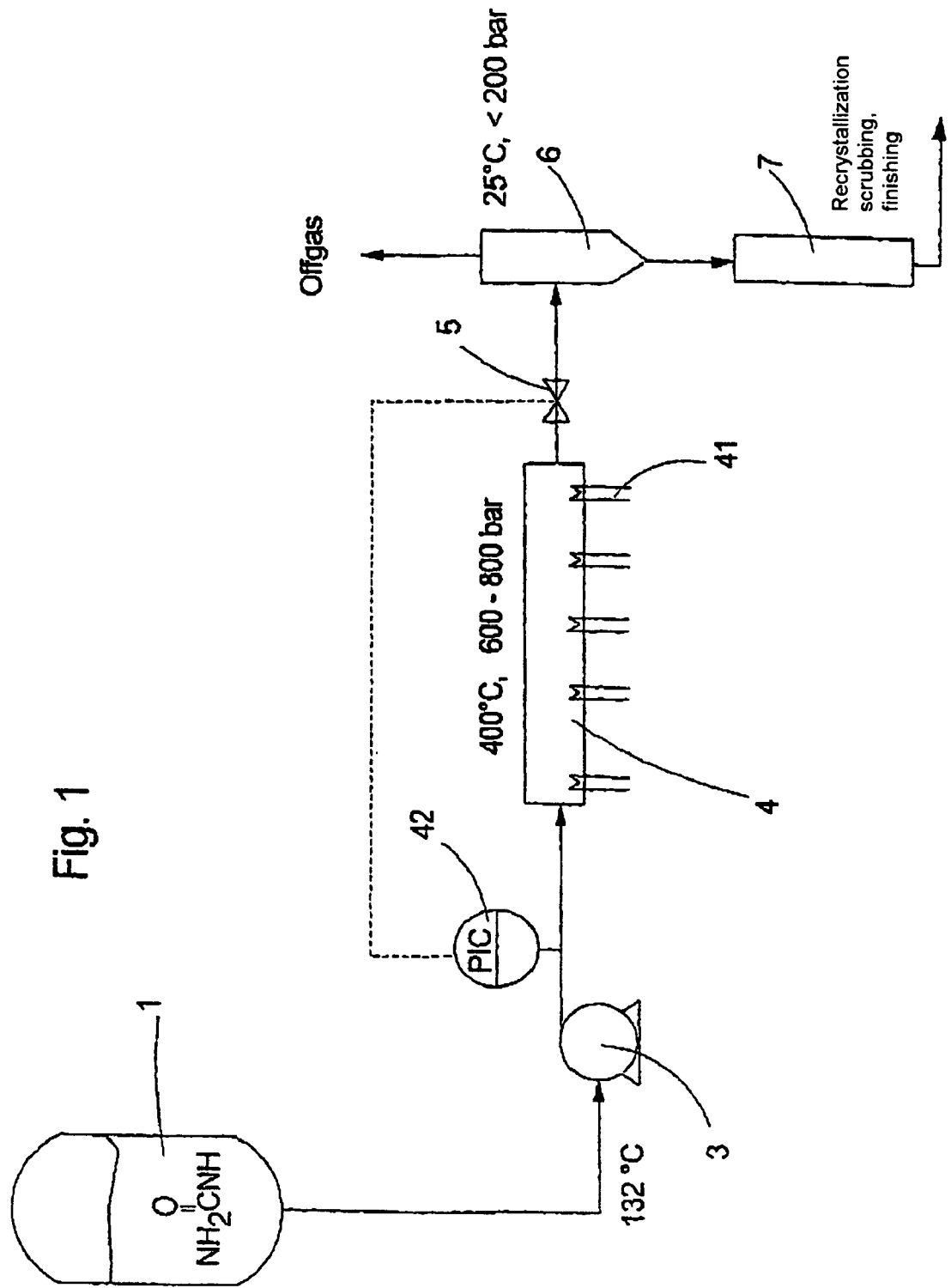

The invention relates to a process according to the preamble of Claim 1 and to an apparatus according to the preamble of Claim 14.

The characteristic substance properties of every pure substance are a critical temperature, a critical pressure and a critical volume. When a substance is in the supercritical state, there no longer exists any division between a liquid phase and a gas phase. The supercritical fluid behaves in a unique manner. For example, a supercritical substance may have a viscosity of a gas at the density of a liquid. The variation of the pressure and of the temperature conditions allows the flow properties of a substance usually to be precisely influenced within wide limits.

In a mixture of supercritical substances (for example ammonia and carbon dioxide) with subcritical substances (depending on temperature, for example, melamine), complete miscibility may lead to mixture properties which correspond to those of supercritical substances. This means that the mixture is in monophasic form.

It is known (see, for example, Ullmann's Encyclopedia of Industrial Chemistry, 5$^{th}$ edition, vol. A16, p. 171 ff) that melamine can be prepared by thermal conversion to melamine according to $$6\ H_2N\text{—}CO\text{—}NH_2 \longrightarrow C_3N_3(NH_2)_3 + 6\ (NH_3) + 3\ CO_2.$$

urea             melamine

In this reaction, molten urea ($T_{melt}$=132° C.) is used. The reaction product obtained is melamine, ammonia and carbon dioxide. Ammonia and carbon dioxide are referred to together as offgas.

In principle, there are two preparation processes for melamine, i.e. noncatalytic, high-pressure processes and catalytic low-pressure processes.

In low-pressure processes, a gas phase reaction is carried out at pressures of typically 10 bar and temperatures between 390 and 410° C. In the high-pressure processes, a liquid phase reaction is carried out at temperatures between 370 to 425° C. and pressures between 70 and 150 bar.

In both process variants, there is the disadvantage that large amounts of offgas are obtained. Since these substances are in the gas phase under the reaction conditions, the reactor in particular has to be designed with appropriately large dimensions. Since the reaction mixture is strongly corrosive, the relatively large reaction vessels have to be manufactured from special material, for example titanium.

Use of a compact tubular reactor under these conditions is not an option, since the offgas very rapidly shifts the unconverted urea out of the reactor. There would be a biphasic reaction mixture. Moreover, the heat transfer under these conditions is poor, so that very large heat transfer surfaces are required in order to introduce the high heat of reaction, which further greatly complicates the reactors.

It is an object of the present invention to provide a process and an apparatus by which a more efficient reaction to give melamine is possible.

This object is achieved in accordance with the invention by a process having the features of Claim 1.

According to the invention, the reaction of urea to melamine proceeds at least partly under reaction conditions under which at least one reactant, intermediate and/or end product is in a supercritical state. The mixture of at least one reactant, intermediate and/or end product also forms a substantially homogeneous phase, and all reactants, intermediates and/or end products are in particular fully dissolved.

The use of a "supercritical mixture" allows monophasicity to be established, by which the reactor volume can be greatly reduced.

This allows material and building space to be saved. This also leads to improvements from a safety viewpoint, since the amount of substance under high pressure is smaller. The high pressure additionally also improves the melamine quality, since the proportion of by-products is reduced. The supercritical substance properties lead, at a corresponding flow rate which is achievable with acceptable pressure drop owing to these substance properties, to a very high heat transfer number, which permits the input of the reaction energy required via the relatively small tube wall surface area.

It is advantageous when the reaction proceeds at least partly at a pressure above 550 bar, in particular between 600 and 800 bar. In an advantageous manner, the reaction proceeds at least partly at a temperature of at least 350° C., in particular 400° C.

In an advantageous embodiment of the process according to the invention, the reaction proceeds in a continuous tubular reactor. It is particularly advantageous when the tubular reactor is at least partly heated to obtain the reaction temperature.

It is also advantageous when liquid urea is used as the reactant.

The attainment of the reaction pressure is advantageously brought about upstream of the reactor by a high-pressure pump which conveys the liquid urea.

In a further advantageous embodiment of the process according to the invention, the reaction product of the reactor is decompressed, to solidify the melamine, into a decompression vessel having a pressure of less than 200 bar, in particular atmospheric pressure.

The decompression from a very high pressure results in distinct cooling. Advantageously, the decompression vessel is heatable.

It may be advantageous when an offgas formed in the decompression vessel has at least the pressure of a urea synthesis, so that it can be fed to a urea synthesis plant.

It is also advantageous when the inventive apparatus has a decompression apparatus, especially a valve for controlled decompression into the decompression vessel.

In addition, it is advantageous when a regulation apparatus for pressure regulation is provided in the reactor, particularly when the regulation apparatus for the reactor pressure is coupled to the decompression apparatus.

The object is also achieved by an apparatus having the features of Claim 13, in which a reactor is designed as a tubular reactor for supercritical reaction conditions. Such a reactor may have a very compact construction.

In an advantageous manner, the tubular reactor comprises a titanium alloy in order to be protected against corrosive media.

It is also advantageous when the inventive apparatus has a decompression apparatus for decompression of reaction products into a decompression vessel.

The invention is illustrated hereinbelow with reference to the figures of the drawings using a working example. The figures show:

FIG. 1 a process flow diagram for a supercritical melamine process;

FIGS. 2a-2d measurements for the change in the volume as a function of the pressure.

FIG. 1 shows one embodiment of the process according to the invention. This is the production of melamine (2,4,6-triamino-1,3,5-triazine, $C_3N_6H_6$) from urea (carbamide, $CO(NH_3)_2$).

To this end, urea is initially charged in a reservoir vessel 1 and fed as required to a reactor 4.

The urea in the reservoir vessel 1 is initially charged at a temperature of somewhat more than 132° C. Subsequently, the urea melt is brought by a high-pressure pump 3 (for example membrane piston pump or gear pump) to a pressure level which is sufficiently high that the subsequent reaction in the reactor 4 can proceed substantially monophasically.

The phase behaviour may be determined by measuring the volume change as a function of the temperature at constant pressure. At low, constant pressures (e.g. 130 bar), i.e. when a biphasic mixture is present, a sharp rise in volume with rising temperature can be seen; a gaseous phase forms. When the same measurement is carried out at a higher pressure (e.g. 800 bar), it can be seen that the volume increase rises with increasing temperature without a sharp increase; no new phase is formed. In addition, the amount of heat required for the heating can be determined in a calorimeter.

In order to achieve monophasicity, the pressure in the reactor 4 will be above 550 bar, preferably in the range from 600 to 800 bar.

To achieve an acceptable conversion, the reactor 4 is heated to at least 350° C., preferably around 400° C. To this end, the reactor 4 is brought to the process temperature over its length using a heater 41. Under these conditions, the reaction mixture is present in a single phase. In this case, the flow is configured as plug flow, so that intensive heat transfer can be established.

The offgases which are otherwise present as a second phase are a portion of the reaction mixture having supercritical material properties. The reactor 4 is configured as a continuous tubular reactor.

Downstream of the reactor 4, the reaction products (melamine, ammonia, carbon dioxide, $NH_2COONH_4$, $NH_2CONH_2$, residues of urea (for example 15%)) are passed via a decompression apparatus 5 into a decompression vessel 6.

The decompression apparatus 5 is configured as a valve. The decompression of the reaction products results in a pressure being formed in the decompression vessel 6. A low pressure may be selected in order to keep the plant costs low, but a pressure of about 200 bar may also be selected, in order to conduct the offgas back into a urea plant. Quenching in, for example, ammonia or water is also conceivable.

The temperature in the decompression vessel 6 may be selected between room temperature and the hydrolysis or decomposition temperature of melamine. The melamine solidifies very rapidly or can be dissolved in the quench medium. The decompression vessel 6 is equipped with a heating apparatus which allows heating or cooling as desired. The heating may influence, for example, the physical state of the melamine, within wide limits.

The valve 5 also serves as the actuator for a regulation apparatus 42 which is configured here as a PI regulator. In principle, other regulation mechanisms, for example multi-parameter regulation systems, may of course also be used. Safety valves or safety regulation systems which are needed under some circumstances are also not shown here.

After the decompression, the gaseous offgases are removed out of the top of the decompression vessel 6. When the decompression vessel 6 is appropriately heated, the carbamate ($NH_2COONH_4$) may be thermally decomposed into carbon dioxide and ammonia (offgas). At a suitable pressure level in the decompression vessel 6, the offgas may be recycled into the high-pressure section of a urea synthesis.

The constituents which are solid or have been taken up in the quench medium (melamine, $NH_2COONH_4$, $NH_2CONH_2$) are discharged from the decompression vessel 6 and are then conducted to a further processing step 7, for example a finishing step or to a recrystallization step not illustrated here in more detail to a scrubbing step.

FIGS. 2a to 2d illustrate measurements which were obtained in the preparation of melamine in the presence of ammonia and carbon dioxide. Each shows the change in the volume as a function of the temperature. The pressure was in each case kept constant.

Figure 2A:
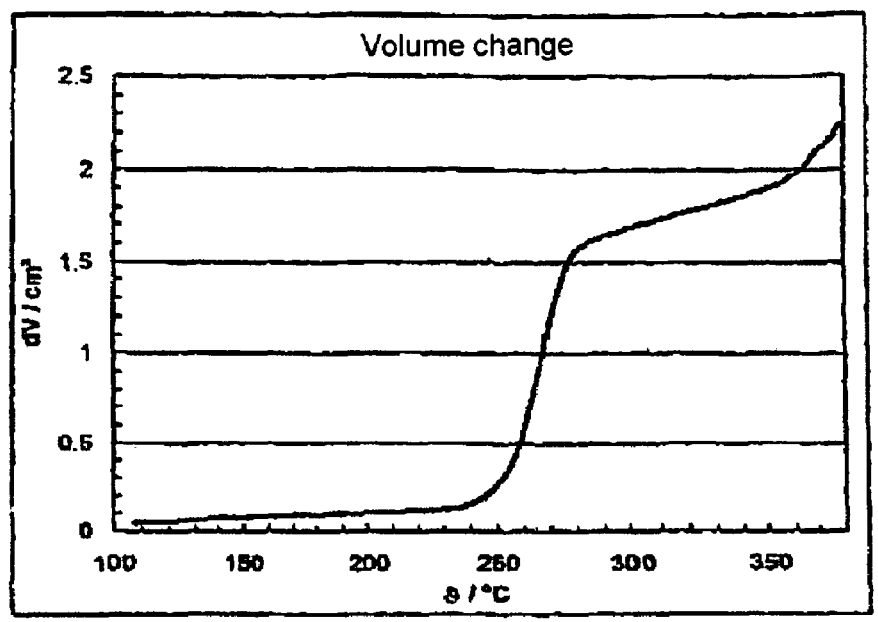
Figure 2B:
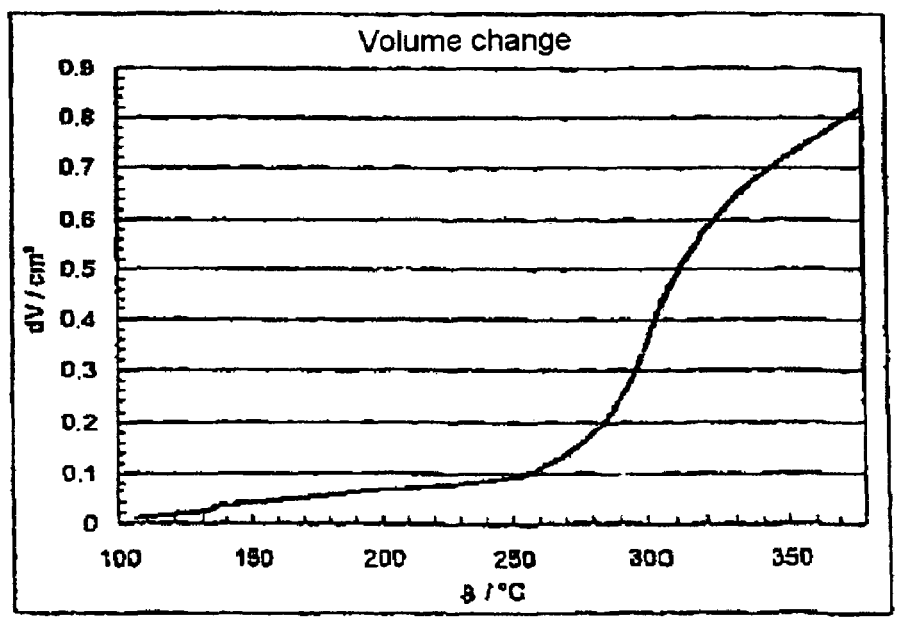
Figure 2C:
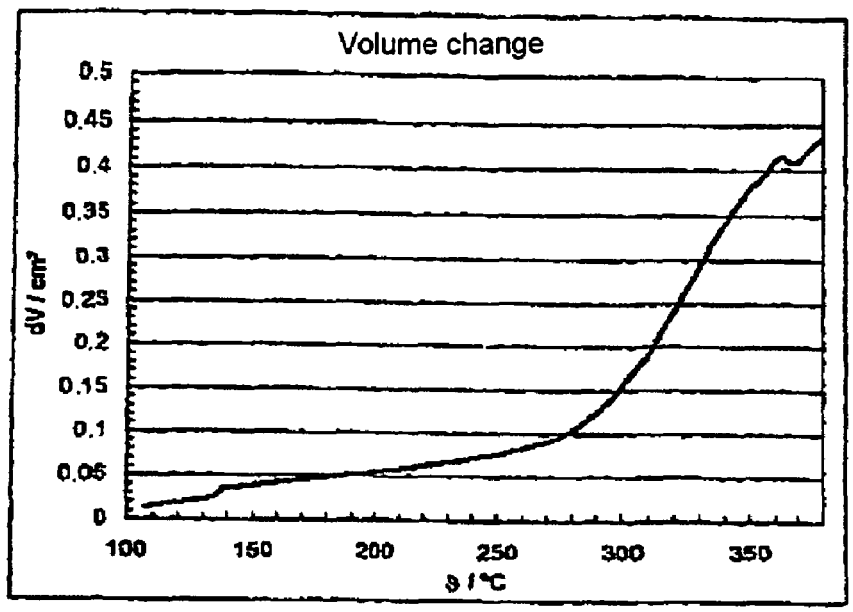

At the lowest pressure of 130 bar (FIG. 2a), it can be seen that there is a great increase in volume above approx. 265° C., i.e. a second, gaseous phase forms. At the next pressure stage of 350 bar (FIG. 2b), the pressure increase above 300° C. is no longer quite so severe; the gradient is lower. This trend continues at 600 bar (FIG. 2c). An evaporation might take place in the range from 300 to 350° C.

Figure 2D:
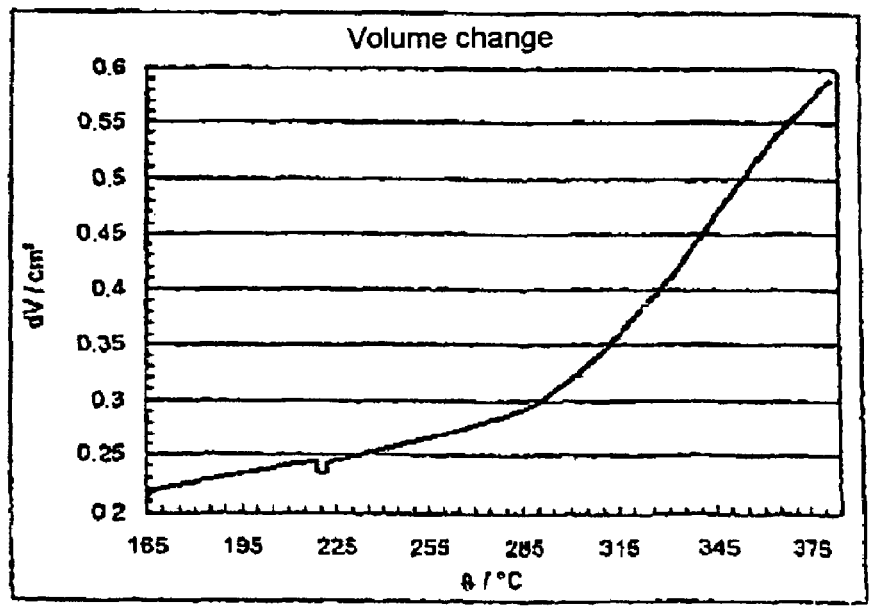

FIG. 2d finally shows the volume increase at a pressure of 800 bar. It is virtually impossible to see an abrupt increase in volume. This shows that the mixture of reactants, intermediates and end products forms a substantially homogeneous mixture whose volume grows relatively constantly with the temperature.

The performance of the invention is not restricted to the above preferred working examples. Rather, a number of variants is conceivable which make use of the process of the invention and of the apparatus of the invention, even in embodiments which are fundamentally of a different nature.

REFERENCE NUMERAL LIST

1 Reservoir vessel
3 High-pressure pump
4 Reactor
5 Decompression apparatus
6 Decompression vessel with heating unit
7 Further processing step

The invention claimed is:

1. A process for preparing melamine by thermally converting urea, wherein
   a) the reaction of urea in a reactor to give melamine proceeds at least partly under reaction conditions under which at least one reactant, intermediate or end product is in a supercritical state, and
   b) the mixture of at least one reactant, intermediate or end product forms a substantially homogeneous phase, and all reactants, intermediates or end products therein are fully dissolved.

2. The process according to claim 1, wherein the reaction proceeds at least partly at a pressure above 550 bar, such as between 600 bar and 800 bar.

3. The process according to claim 1, wherein the reaction proceeds at least partly at a temperature of at least 350° C., such as at 400° C.

4. The process according to claim 1, wherein the reaction is carried out in a continuous tubular reactor.

5. The process according to claim 4, wherein the tubular reactor is at least partly heated.

6. The process according to claim 1, wherein urea is used as a liquid reactant.

7. The process according to claim 1, wherein the reactant is brought to a required reaction pressure upstream of the reactor by a high-pressure pump.

8. The process according to claim 1, wherein a reaction product of the reactor is decompressed to solidify the melamine in a decompression vessel having a pressure below 200 bar, such as atmospheric pressure.

9. The process according to claim 8, wherein an offgas formed in the decompression vessel has at least the pressure of a urea synthesis so that it can be fed to a urea synthesis plant.

10. The process according to claim 9, wherein the decompression vessel is heated.

11. The process according to claim 10, wherein the reaction product is passed by a decompression apparatus, such as a valve for controlled decompression, before entry into the decompression vessel.

12. The process according to claim 1, wherein a regulation apparatus for pressure regulation is present in the reactor.

13. The process according to claim 11, wherein the regulation apparatus for the reactor pressure is coupled to the decompression apparatus.

14. An apparatus for carrying out the process according to claim 1, wherein the reactor is a tubular reactor for supercritical reaction conditions.

15. The apparatus according to claim 14, wherein the tubular reactor comprises a titanium alloy.

16. The apparatus according to claim 14, wherein the reaction product is passed by a decompression apparatus for decompression of reaction products before entry into a decompression vessel.

17. The process according to claim 2, wherein the reaction proceeds at least partly at a temperature of at least 350° C., such as at 400° C.

18. The process according to claim 2, wherein the reaction is carried out in a continuous tubular reactor.

19. The process according to claim 3, wherein the reaction is carried out in a continuous tubular reactor.

20. The process according to claim 2, wherein the reactant is brought to a required reaction pressure upstream of the reactor by a high-pressure pump.

21. The process according to claim 3, wherein the reactant is brought to a required reaction pressure upstream of the reactor by a high-pressure pump.

* * * * *